(12) United States Patent
Skarda

(10) Patent No.: US 7,104,989 B2
(45) Date of Patent: Sep. 12, 2006

(54) RF ABLATION CATHETER INCLUDING A VIRTUAL ELECTRODE ASSEMBLY

(75) Inventor: James R. Skarda, Lake Elmo, MN (US)

(73) Assignee: Medtronic, Inc., Minneapolis, MN (US)

( * ) Notice: Subject to any disclaimer, the term of this patent is extended or adjusted under 35 U.S.C. 154(b) by 251 days.

(21) Appl. No.: 10/656,422

(22) Filed: Sep. 5, 2003

(65) Prior Publication Data

US 2005/0055019 A1    Mar. 10, 2005

(51) Int. Cl.
    *A61B 18/18* (2006.01)
(52) U.S. Cl. ............ 606/41; 606/48; 606/49; 606/50; 607/101; 607/102; 607/103; 607/104; 607/105
(58) Field of Classification Search ........... 606/41, 606/48–50; 607/101–105
    See application file for complete search history.

(56) References Cited

U.S. PATENT DOCUMENTS

| | | | |
|---|---|---|---|
| 4,532,924 A * | 8/1985 | Auth et al. ............ 606/50 |
| 5,047,028 A * | 9/1991 | Qian ................. 606/49 |
| 5,643,197 A * | 7/1997 | Brucker et al. ........ 604/20 |
| 5,846,239 A * | 12/1998 | Swanson et al. ........ 606/41 |
| 5,913,856 A * | 6/1999 | Chia et al. ........... 606/41 |
| 5,919,188 A * | 7/1999 | Shearon et al. ........ 606/41 |
| 6,056,747 A * | 5/2000 | Saadat et al. .......... 606/50 |
| 6,071,278 A | 6/2000 | Panescu et al. |
| 6,076,012 A * | 6/2000 | Swanson et al. ........ 604/21 |
| 6,119,041 A * | 9/2000 | Pomeranz et al. ....... 607/101 |
| 6,120,476 A | 9/2000 | Fung et al. |
| 6,171,275 B1 | 1/2001 | Webster, Jr. |
| 6,277,089 B1 * | 8/2001 | Yoon ................. 604/1 |
| 6,466,818 B1 | 10/2002 | Moaddeb et al. |
| 6,497,705 B1 | 12/2002 | Comben |
| 6,522,930 B1 | 2/2003 | Schaer et al. |
| 6,537,272 B1 | 3/2003 | Christopherson et al. |
| 6,602,242 B1 | 8/2003 | Fung et al. |
| 6,673,068 B1 * | 1/2004 | Berube ............... 606/33 |
| 2002/0128640 A1 * | 9/2002 | Swanson ............. 606/32 |
| 2003/0014048 A1 * | 1/2003 | Swanson ............. 606/41 |

* cited by examiner

*Primary Examiner*—Michael Peffley
*Assistant Examiner*—Alex Toy
(74) *Attorney, Agent, or Firm*—Michael C. Soldner; Girma Wolde-Michael

(57) ABSTRACT

A virtual ablation electrode assembly includes a non-conductive outer cap fitted over an inner electrode to form a fluid chamber between a cap inner surface and an exterior surface of the electrode. The inner electrode includes an interior fluid trunk and one or more fluid distribution branches extending from the fluid trunk to the exterior surface. A plurality of pores extends between the cap inner surface and a cap outer surface. When the electrode is energized and when fluid is delivered through the one or more fluid distribution branches from the trunk, the conductive fluid fills the fluid chamber and flows out from the chamber through the plurality of pores of the cap establishing ionic transport of ablation energy from the inner electrode to a target site in close proximity to the cap.

44 Claims, 4 Drawing Sheets

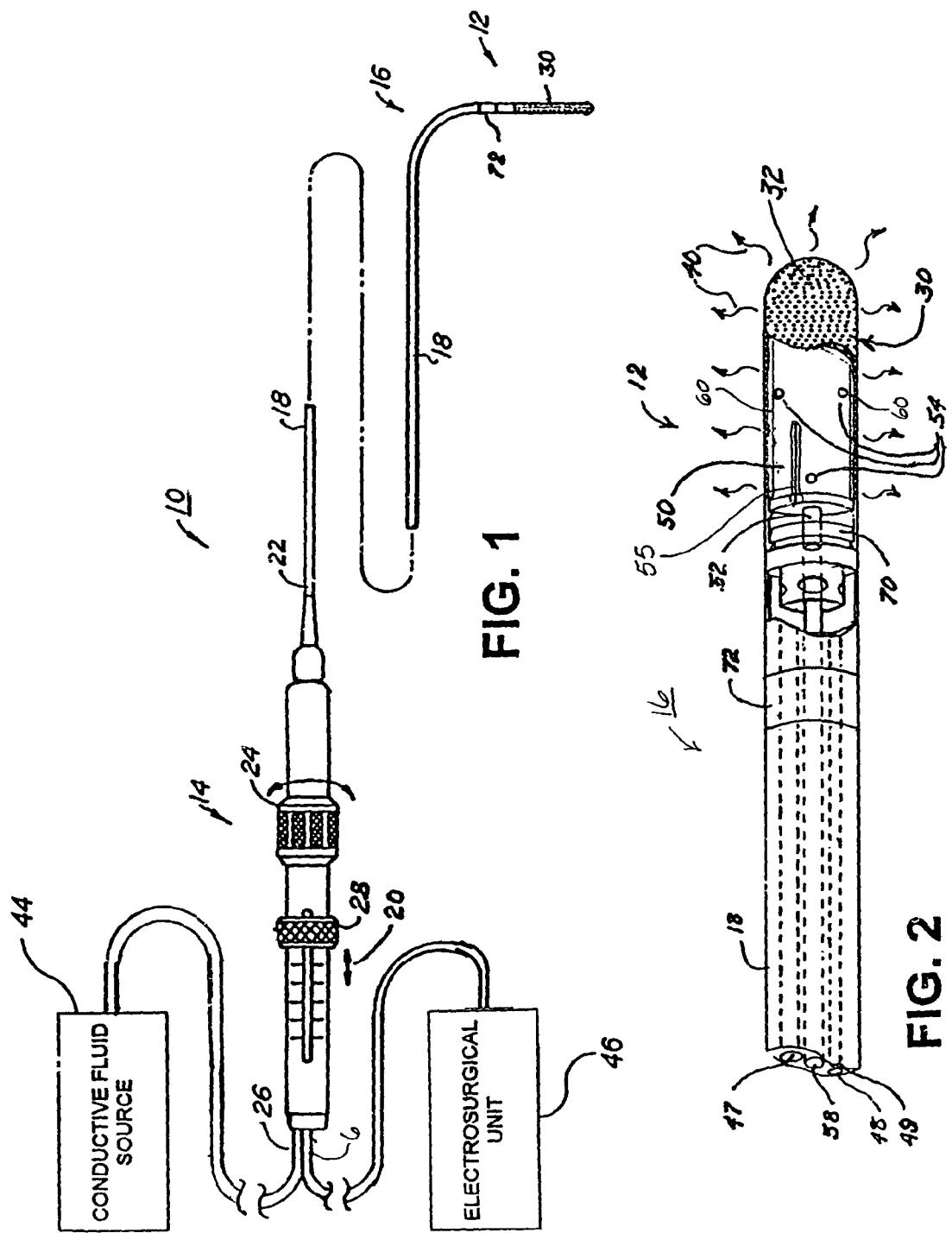

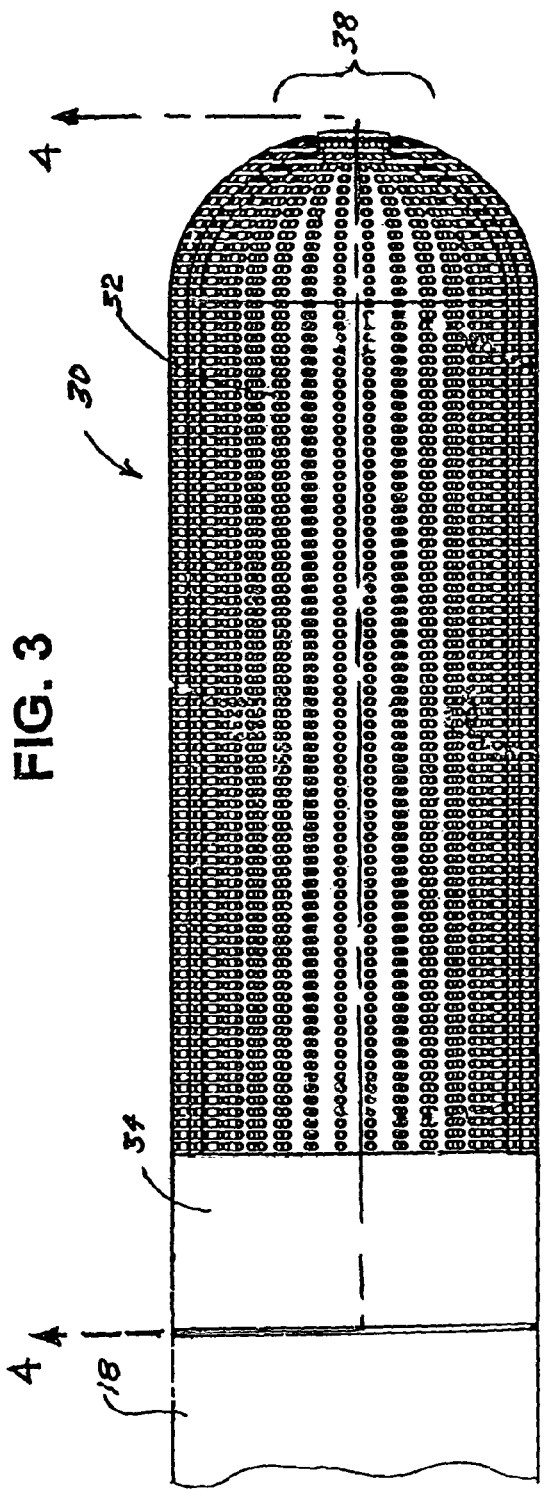
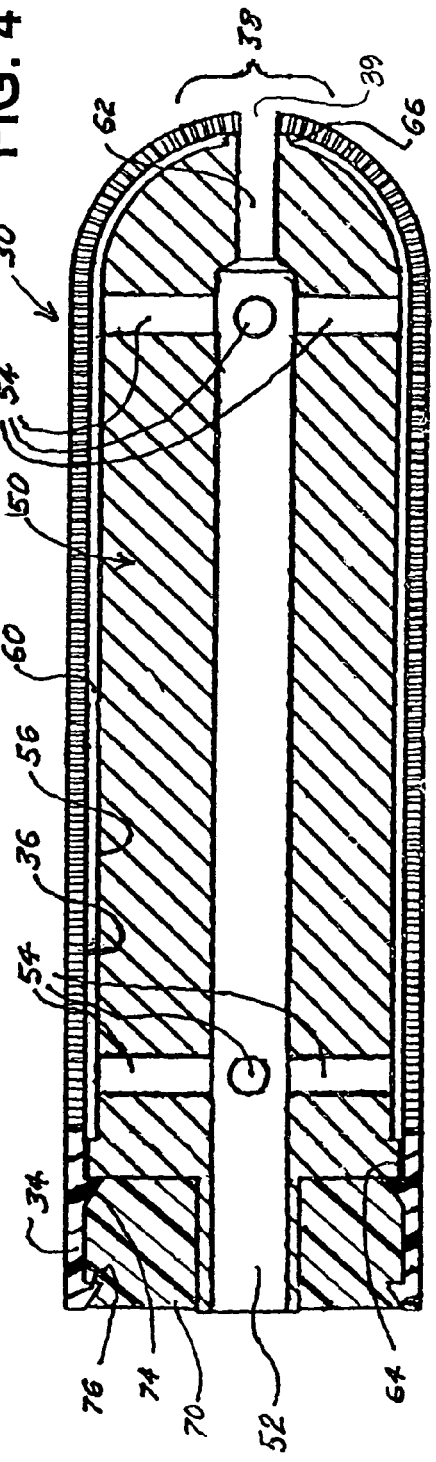

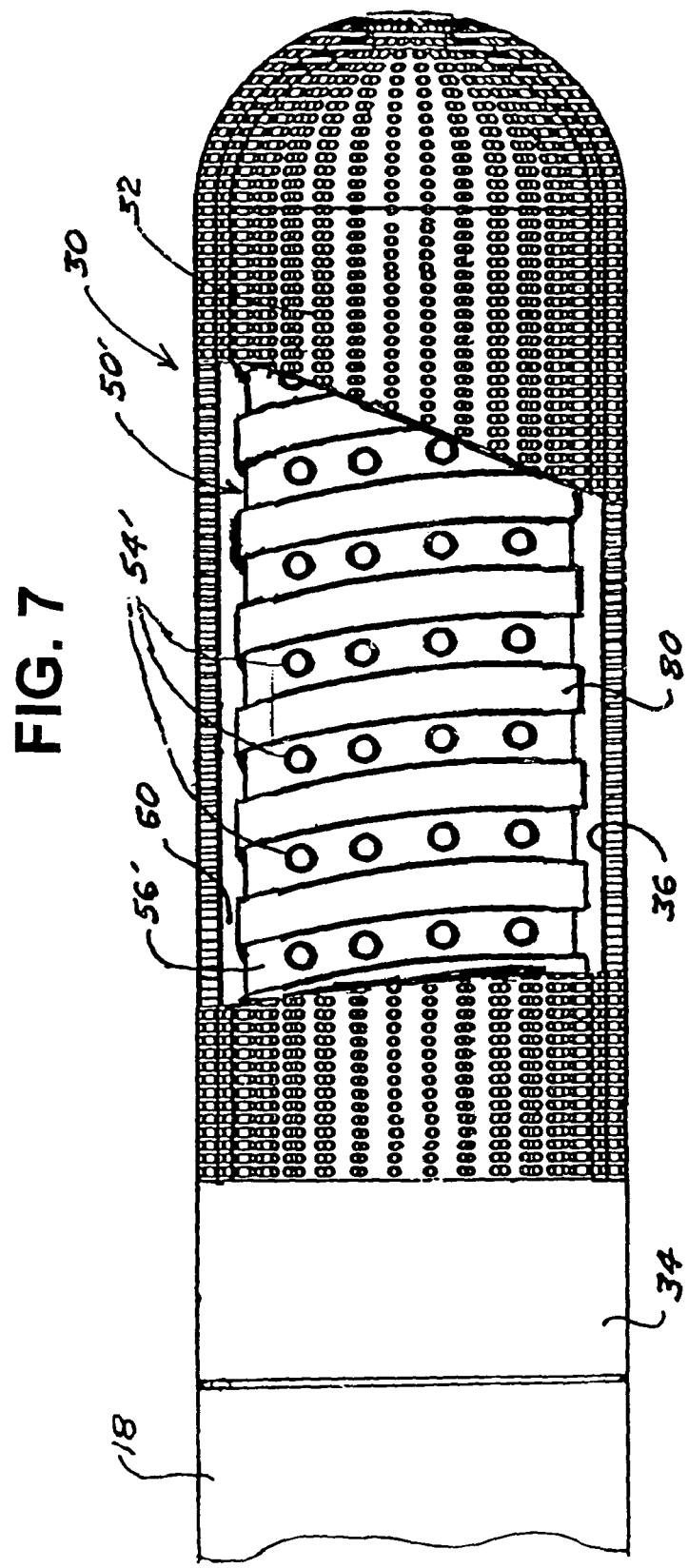

ered RF ablation catheter # RF ABLATION CATHETER INCLUDING A VIRTUAL ELECTRODE ASSEMBLY

TECHNICAL FIELD

The present invention relates generally to an electrophysiology (EP) catheter for use in radiofrequency (RF) ablation, particularly an RF ablation catheter including a virtual electrode delivering ablation energy through conductive fluid emitted from a porous tip.

BACKGROUND

Therapies have been developed for treating atrial and ventricular tachycardias by destroying cardiac tissue containing an identified ectopic foci or an aberrant conduction pathway; one of these therapies includes the application of ablative RF energy delivered through a catheter, which may be introduced transvenously into the heart, to a target site via a virtual electrode formed by conductive fluid infused out from a portion of the catheter in proximity to the site. An ablation electrode contained within that portion of the catheter and shielded by a non-conductive porous shell energizes the infused fluid; the rate of infusion and conductivity of the fluid can be controlled to work in conjunction with various electrodes with different surface areas. The creation of the virtual electrode enables the current to flow with reduced resistance or impedance throughout a larger volume of tissue, thus spreading the resistive heating created by the current flow through a larger volume of tissue and thereby creating a larger lesion than could otherwise be created with a 'dry' electrode. Furthermore, virtual electrodes reduce the potential for complications arising from an excessive electrode temperature (approximately greater than 100 degrees Celsius), typically associated with 'dry' ablation electrodes in direct contact with the target site, which may cause formation of blood coagulum and sub-surface explosions or pops within the tissue.

Physicians have long used the technique of pressing an RF electrode, which terminates a distal end of a catheter, against the endocardium, applying RF energy, and dragging the electrode along the endocardium to create an elongated lesion. Consequently, there remains a need for an improved RF ablation catheter including a virtual electrode assembly that is simple to fabricate and to use efficaciously in this manner.

BRIEF DESCRIPTION OF THE DRAWINGS

The following drawings are illustrative of particular embodiments of the invention and therefore do not limit its scope, but are presented to assist in providing a proper understanding of the invention. The drawings are not to scale (unless so stated) and are intended for use in conjunction with the explanations in the following detailed description. The present invention will hereinafter be described in conjunction with the appended drawings, wherein like numerals denote like elements, and:

FIG. 1 is a schematic over-view of an ablation system according to one embodiment of the present invention;

FIG. 2 is an enlarged plan view with partial section detailing a distal portion of the ablation catheter shown in FIG. 1;

FIG. 3 is an enlarged plan view of a virtual electrode assembly according to an embodiment of the present invention;

FIG. 4 is a cross-section view along section line 4—4 shown in FIG. 3;

FIG. 7 is a plan view with partial section of a virtual electrode assembly according to an alternate embodiment of the present invention.

DETAILED DESCRIPTION

Figure 5:
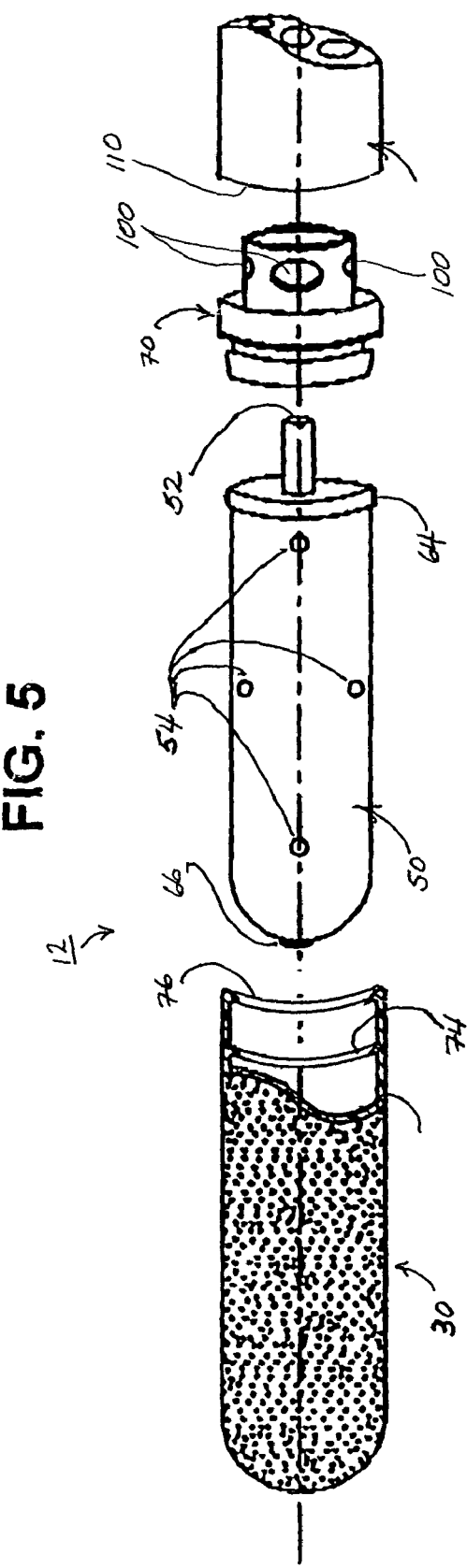
FIG. 5 is an exploded perspective view of a virtual electrode assembly according to one embodiment of the present invention.

The following detailed description is exemplary in nature and is not intended to limit the scope, applicability, or configuration of the invention in any way. Rather, the following description provides a practical illustration for implementing exemplary embodiments of the invention.

FIG. 1 is a schematic over-view of an ablation system according to one embodiment of the present invention. FIG. 1 illustrates the ablation system including an RF ablation catheter 10 an electro-surgical unit 46, which includes an RF energy source, and a conductive fluid source 44; ablation catheter 10 includes an elongated, flexible, catheter shaft or body 18 extending from a distal virtual electrode assembly 12, coupled to a distal segment 16 of body 18, to a proximal handle 14, which couples catheter 10 to electro-surgical unit 46, via electrical terminals 6, and to conductive fluid source 44, via a port 26. FIG. 1 further illustrates catheter 10 including one or more ring-shaped mapping electrodes 72 positioned about body 18 proximal to virtual electrode 12. Catheter body 18 may be of any suitable diameter and length and may be straight or pre-curved along its length. According to one embodiment, catheter body 18 has a uniform outside diameter of about 0.052 inch (1.32 mm) to about 0.1040 inch (2.64 mm) and a length of about 50 cm to about 110 cm. Catheter body 18 may be formed in any of the manners known in the art to include a plurality of lumens (FIG. 2) extending from handle 14 to catheter body distal segment 16 accommodating fluid delivery, electrical conductors, push-pull wire(s), and a torque wire, for example.

Handle 14 coupled to a proximal end 22 of the catheter body 18, as illustrated in FIG. 1, may take any of the forms known in the art and includes a mechanism for deflecting a distal segment of the catheter body 18 into a curve to facilitate transvenous introduction of virtual electrode assembly 12 into a heart chamber and then directing it to a target ablation site. The mechanism illustrated in FIG. 1 includes an axially slidable ring 28 coupled to a proximal end of a curve deflection push-pull wire (not shown) and a rotatable lateral deflection or torque ring 24 coupled to a proximal end of a lateral deflection wire (not shown); torque ring 24 may be rotated to impart a torque in the lateral deflection wire coupled thus rotating distal segment 16 with respect to a longitudinal axis of catheter body 18.

FIG. 2 is an enlarged plan view with partial section detailing a distal end of distal segment 16 of ablation catheter 10 shown in FIG. 1. FIG. 2 illustrates virtual electrode assembly 12 terminating the distal end of distal segment 16 and including a non-conductive, outer cap 30 fixed over an inner electrode 50; according to embodiments of the present invention a fluid chamber 60, facilitating ionic charging of conductive fluid, having fixed dimensions is maintained between an outer surface of electrode 50 and an inner surface of outer cap 30. As is further illustrated in FIG. 2, catheter body 18 includes a fluid lumen 58 in fluid communication with an interior fluid trunk 52 of electrode 50 through which the conductive fluid is delivered (from fluid source 44 illustrated in FIG. 1); the conductive fluid then passes through a plurality of radially extending fluid distribution branches 54 extending from fluid trunk 52 to an exterior surface 56 (FIG. 4) of electrode 50 to fill chamber 60 and perfuse, as a charged conductive fluid 40, out from virtual electrode assembly 12 through a plurality of pores 32 extending though a wall 34 of outer cap 30. The conductive fluid, thus establishes ionic transport of ablation energy from electrode 50 to a target site in close proximity to outer cap 30; one example of an appropriate conductive fluid comprises a hypertonic saline solution. FIG. 2 further illustrates a thermocouple 55 positioned in proximity to the exterior surface of electrode 50 in order to monitor the temperature of fluid filling chamber 60; according to one embodiment a groove is formed in the exterior surface of electrode 50 to hold thermocouple 55.

FIG. 3 is an enlarged plan view of a virtual electrode assembly according to an embodiment of the present invention. FIG. 3 illustrates plurality of pores 32 arrayed longitudinally and circumferentially around all sides of cap 30, including a dome-shaped distal end region 38, to enable emission of the conductive fluid out from cap 30 both in a 360° pattern around a circumference of cap 30, along a length of cap 30, and axially out from distal end region 38 of cap 30. Alternately, distal end region 38 may be a more blunt shape or a more tapered shape. In one exemplary embodiment, cap 30 is about 0.3 inch in length, about 0.09 inch in outer diameter, and about 0.08 inch in inner diameter; pores 32 are sized to allow passage of charged conductive fluid 40 (FIG. 2) while preventing external blood platelets and proteins from blocking pores 32 or entering fluid chamber 60 (FIG. 2), according to one embodiment, but are larger, for example between 0.0005 inch and 0.005 inch according to an alternate embodiment. Pores 32 may be formed through cap wall 34, for example, by laser drilling, chemical etching or sintering, in a uniform pattern as illustrated or in a more random pattern; furthermore pore sizes among plurality of pores 32 may be uniform or vary. Cap 30 may be formed of a rigid plastic, such as PEEK, or of a ceramic; in any case cap 30 is preferably a biocompatible material resistant to high temperatures associated with RF ablation, additional examples of which include but are not limited to injection grade plastics, fluoropolymers, such as PTFE, e-PTFE, and FEP.

FIG. 4 is a cross-section view along section line 4—4 shown in FIG. 3. FIG. 4 illustrates electrode 50 including fluid trunk 52, radially extending fluid branches 54 and a distally extending fluid branch 62 to deliver conductive fluid to fluid chamber 60 formed between exterior surface 56 of electrode 50 and an inner surface 36 of cap 30 from which charged conductive fluid 40 (FIG. 2) is emitted through pores 32. Electrode 50 may be formed from any appropriate electrode material examples of which include, but are not limited to, stainless steels and platinum-iridium alloys. According to various embodiments a diameter of trunk 52 ranges between approximately 0.005 inch approximately 0.030 inch and diameters of branches 54, 62 range between approximately 0.005 inch and approximately 0.030 inch; the trunk and branch diameters may be varied according to various performance requirements requiring different distributions of fluid flow.

Figure 6:
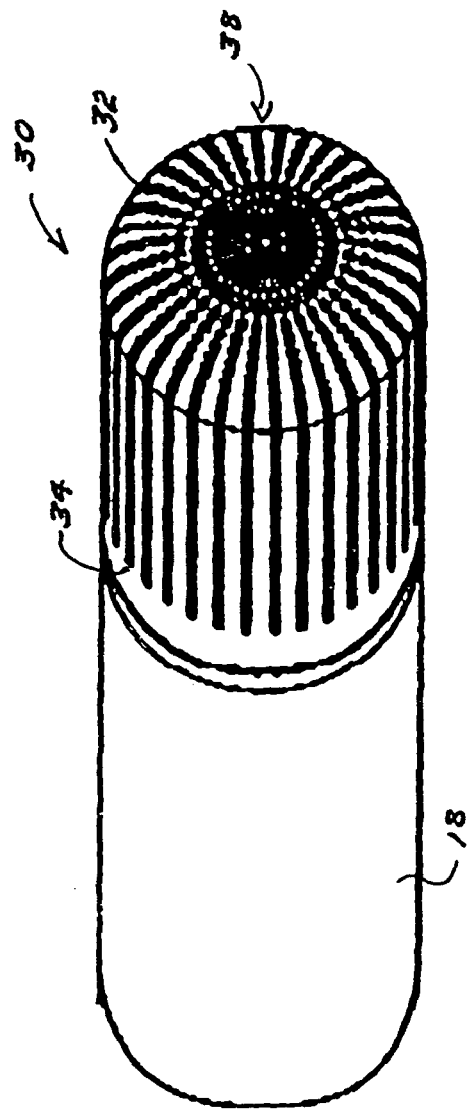
FIG. 6 is a perspective end view of a virtual electrode according to an embodiment of the present invention.

As further illustrated in FIG. 4, electrode 50 also includes a proximal spacer 64, extending circumferentially about, and outward from exterior surface 56, and a distal spacer 66, extending distally from exterior surface 56 at a distal end of electrode 50. According to embodiments of the present invention spacers 64, 66 contact an inner surface 36 of outer cap 30 as means to maintain a fixed, annular, fluid chamber 60 between exterior surface 56 of electrode 50 and inner surface 36 of outer cap 30 facilitating ionic charging of conductive fluid by RF energy delivered to electrode 50. Thus, virtual electrode assembly 12 results a consistent volume, fixed fluid chamber 60 providing a consistent emission of charged conductive fluid 40 through pores 32 of outer cap 30. According to an exemplary embodiment, a width of chamber 60 (a maximum distance between exterior surface 56 of electrode 50 and inner surface 36 of cap 30) is between approximately 0.003 inch and approximately 0.005 inch. Although FIG. 4 illustrates distally extending fluid branch extending through distal spacer in fluid communication with a larger hole 39 through wall 34 of end cap 30, according to an alternate embodiment, as illustrated in FIG. 6 pores 32 extend over this region.

FIG. 4 further illustrates outer cap 30 including a first detent 74 and a second detent 76; according to embodiments of the present invention first detent 74 serves to couple cap 30 to electrode 50 by engaging proximal spacer 64 while second detent 76 serves as means to couple cap 30 and electrode 50 to catheter body 18 by engaging a connector ring 70, which is coupled to catheter body 18 as illustrated in FIG. 2. According to an alternate embodiment outer cap 30 is coupled to electrode 50 by means of a friction fit with proximal spacer 64 and/or other spacers extending outward from exterior surface 56 of electrode 50.

Referring back to FIGS. 1 and 2, according to one embodiment, a push-pull wire (not shown) extends from a connection with connector ring 70 through a lumen 47 of body 18 to a connection with slide ring 28 on handle 14 and a torque wire (not shown) extends from a connection with connector ring 70 through a lumen 48 to a connection with torque ring 24 on handle 14. Furthermore, electrode 50, thermocouple 55 and one or more mapping electrodes 72 are coupled to electro-surgical unit 46 via electrical conductors (not shown) extending through a lumen 49 of catheter body 18 to a connection with electrical terminals 6 of handle 14.

FIG. 5 is an exploded perspective view of a virtual electrode assembly according to one embodiment of the present invention. According to embodiments of the present invention, FIG. 5 illustrates means by which virtual electrode assembly is assembled onto catheter body 18, wherein connector ring 70 is fitted into a distal end 110 of body 18, electrode 50 is fitted into connector ring, and cap 30 is fitted over electrode 50 and a distal portion of connector ring 70. Electrical conductors, push-pull wire, and torque wire are coupled to ring 70 via crimping, welding or other means known to those skilled in the art, and ring 70 is coupled to catheter body 18 via interlocking material, such as adhesive, bonding to catheter body and interlocking within ports 100 of ring; electrode 50 may be coupled to ring 70 prior to or after coupling with catheter body 18 in a manner providing electrical coupling between conductors delivering RF energy and electrode 50, e.g. welding. Cap 30 is assembled over electrode 50 and pushed proximally until second detent 76 engages ring 70 and first detent engages proximal spacer 64. Finally, a tubing band in conjunction with adhesive bonding or ultrasonic welding may be employed to secure the junction between electrode assembly 12 and catheter body 18.

FIG. 6 is a perspective end view of a virtual electrode according to an embodiment of the present invention wherein a density of pores 32 is increased in distal end region 38 of cap 30, thus concentrating delivery of conductive fluid 40 distally to facilitate both a formation of a discrete lesion and a formation of an elongated lesion by means of pushing or dragging distal end region 38 over the tissue to be ablated.

FIG. 7 is a plan view with partial section of a virtual electrode assembly according to an alternate embodiment of the present invention. FIG. 7 illustrates an exterior surface 56' of an electrode 50' including extensions formed as ridges or a spiral coil 80 as means to increase an exterior surface area of electrode 50'. FIG. 7 further illustrates an alternative spiral pattern of fluid branches 54' extending from an interior fluid trunk, e.g. trunk 52 shown in FIG. 4, to exterior surface 56' within spiral valleys between turns of spiral coil 80.

It will be understood that certain of the above-described structures, functions and operations of the above-described embodiments are not necessary to practice the present invention and are included in the description simply for completeness of an exemplary embodiment or embodiments. Thus, it is expected that various changes, alterations, or modifications may be made to the invention as described herein without departing from the spirit and scope of the invention as defined by the appended claims.

What is claimed is:

1. An ablation catheter comprising:
   an elongated catheter body extending between a catheter body proximal end and a catheter body distal end, the elongated catheter body including elongated electrical conductors extending between the catheter body proximal end and the catheter body distal end, a fluid port positioned in proximity to the catheter body proximal end and a fluid delivery lumen extending between the port and the catheter body distal end; and
   a virtual electrode assembly terminating the catheter body distal end and including an inner electrode electrically coupled to the elongated conductors, a non-conductive outer cap fixed over the electrode and a fluid chamber formed between the inner electrode and the outer cap;
   wherein the outer cap includes a cap inner surface, a cap outer surface and a plurality of pores extending between the cap inner surface and the cap outer surface;
   the inner electrode includes an interior fluid trunk in fluid communication with the fluid delivery lumen of the catheter body, an exterior surface, one or more fluid distribution branches extending from the fluid trunk to the exterior surface, and one or more spacers protruding from the exterior surface and contacting the cap inner surface to maintain the fluid chamber between the inner electrode and the outer cap;
   a connector ring facilitating coupling of the virtual electrode assembly to the catheter body distal end;
   means for coupling the outer cap to the electrode assembly by engaging the one or more spacers of the inner electrode; and
   when the inner electrode is energized, via the elongated conductor, and a conductive fluid is delivered through the one or more fluid distribution branches from the fluid trunk, supplied by the fluid delivery lumen of the catheter, the conductive fluid fills the fluid chamber and flows out from the chamber through the plurality of pores of the cap establishing ionic transport of ablation energy from the inner electrode to a target site in close proximity to the cap.

2. The ablation catheter of claim 1, wherein the outer cap further includes a dome-shaped distal end region.

3. The ablation catheter of claim 1, wherein the coupling means comprises one or more detents on the outer cap engaging the one or more spacers of the inner electrode.

4. The ablation catheter of claim 1, wherein the outer cap further includes a detent engaging the connector ring.

5. The ablation catheter of claim 1, wherein the outer cap is formed of a material comprising a rigid plastic.

6. The ablation catheter of claim 1, wherein the outer cap is formed of a material comprising a fluoro-polymer.

7. The ablation catheter of claim 1, wherein the outer cap is formed of a material comprising an epoxy resin.

8. The ablation catheter of claim 1, wherein the plurality of pores are arrayed longitudinally along a length of the outer cap and circumferentially 360 degrees around the outer cap.

9. The ablation catheter of claim 1, wherein the plurality of pores are arrayed longitudinally along a length of the outer cap and circumferentially 360 degrees around the outer cap extending over the dome-shaped distal end region.

10. The ablation catheter of claim 1, wherein a maximum diameter of each of the plurality of pores is sized to prevent ingress of blood cells into the fluid chamber from the cap outer surface.

11. The ablation catheter of claim 1, wherein a maximum diameter of each of the plurality of pores is between approximately 0.0005 inch and 0.005 inch.

12. The ablation catheter of claim 1, wherein the plurality of pores is formed by a process selected from the group consisting of laser drilling, chemical etching and sintering.

13. The ablation catheter of claim 1, wherein the exterior surface of the electrode includes extensions increasing a surface area of the exterior surface.

14. The ablation catheter of claim 13, wherein the extensions form a spiral coil.

15. The ablation catheter of claim 1, wherein the one or more spacers extend circumferentially about a proximal end of the electrode.

16. The ablation catheter of claim 1, wherein the one or more spacers extend distally from a distal end of the electrode.

17. The ablation catheter of claim 1, wherein one of the one or more fluid distribution branches passes through a distal end of the electrode.

18. The ablation catheter of claim 17, wherein the one of the one or more spacers extends distally from a distal end of the electrode.

19. The ablation catheter of claim 18, wherein the cap further includes a hole extending from the cap inner surface to the cap outer surface and generally aligned and in fluid communication with the one of the one or more fluid distribution branches.

20. The ablation catheter of claim 1, wherein a diameter of the fluid trunk of the electrode is between approximately 0.005 inch and approximately 0.030 inch.

21. The ablation catheter of claim 1, wherein a diameter of each of the one or more fluid distribution branches is between approximately 0.005 inch and approximately 0.030 inch.

22. An ablation catheter comprising:
   an elongated catheter body extending between a catheter body proximal end and a catheter body distal end, the elongated catheter body including elongated electrical conductors extending between the catheter body proximal end and the catheter body distal end, a fluid port positioned in proximity to the catheter body proximal end and a fluid delivery lumen extending between the port and the catheter body distal end; and
   a virtual electrode assembly terminating the catheter body distal end and including an inner electrode electrically coupled to the elongated conductors, a non-conductive outer cap fixed over the electrode and a fluid chamber formed between the inner electrode and the outer cap;

wherein the outer cap includes a cap inner surface, a cap outer surface and a plurality of pores extending between the cap inner surface and the cap outer surface;

the inner electrode includes an interior fluid trunk in fluid communication with the fluid delivery lumen of the catheter body, an exterior surface, one or more fluid distribution branches extending from the fluid trunk to the exterior surface, and one or more spacers protruding from the exterior surface and contacting the cap inner surface to maintain the fluid chamber between the inner electrode and the outer cap;

means for coupling the outer cap to the electrode assembly by engaging the one or more spacers of the inner electrode; and when the inner electrode is energized, via the elongated conductor, and a conductive fluid is delivered through the one or more fluid distribution branches from the fluid trunk, supplied by the fluid delivery lumen of the catheter, the conductive fluid fills the fluid chamber and flows out from the chamber through the plurality of pores of the cap establishing ionic transport of ablation energy from the inner electrode to a target site in close proximity to the cap, wherein the outer cap is formed of a material comprising a ceramic.

23. An ablation catheter comprising:

an elongated catheter body extending between a catheter body proximal end and a catheter body distal end, the elongated catheter body including elongated electrical conductors extending between the catheter body proximal end and the catheter body distal end, a fluid port positioned in proximity to the catheter body proximal end and a fluid delivery lumen extending between the port and the catheter body distal end; and a virtual electrode assembly terminating the catheter body distal end and including an inner electrode electrically coupled to the elongated conductors, a non-conductive outer cap fixed over the electrode and a fluid chamber formed between the inner electrode and the outer cap;

wherein the outer cap includes a cap inner surface, a cap outer surface and a plurality of pores extending between the cap inner surface and the cap outer surface;

the inner electrode includes an interior fluid trunk in fluid communication with the fluid delivery lumen of the catheter body, an exterior surface, one or more fluid distribution branches extending from the fluid trunk to the exterior surface, and one or more spacers protruding from the exterior surface and contacting the cap inner surface to maintain the fluid chamber between the inner electrode and the outer cap;

means for coupling the outer cap to the electrode assembly by engaging the one or more spacers of the inner electrode; and when the inner electrode is energized, via the elongated conductor, and a conductive fluid is delivered through the one or more fluid distribution branches from the fluid trunk, supplied by the fluid delivery lumen of the catheter, the conductive fluid fills the fluid chamber and flows out from the chamber through the plurality of pores of the cap establishing ionic transport of ablation energy from the inner electrode to a target site in close proximity to the cap, wherein a maximum distance between the exterior surface of the electrode and the cap inner surface is between approximately 0.003 inch and approximately 0.005 inch.

24. A virtual ablation electrode assembly, comprising:

a non-conductive outer cap including a cap inner surface, a cap outer surface and a plurality of pores extending between the cap inner surface and the cap outer surface;

an inner electrode including an interior fluid trunk, an exterior surface, one or more fluid distribution branches extending from the fluid trunk to the exterior surface, and one or more spacers protruding from the exterior surface and contacting the cap inner surface;

means for coupling the outer cap to the electrode assembly by engaging the one or more spacers of the inner electrode; and a fluid chamber formed between the inner electrode and the outer cap and maintained by the one more spacers;

wherein, when the electrode is energized and when fluid is delivered through the one or more fluid distribution branches from the trunk, the conductive fluid fills the fluid chamber and flows out from the chamber through the plurality of pores of the cap establishing ionic transport of ablation energy from the inner electrode to a target site in close proximity to the cap, and wherein the coupling means comprises one or more detents on the outer cap engaging the one or more spacers of the inner electrode.

25. The virtual ablation electrode assembly of claim 24, wherein the outer cap further includes a dome-shaped distal end region.

26. The virtual ablation electrode assembly of claim 24, wherein the outer cap is formed of a material comprising a rigid plastic.

27. The virtual ablation electrode assembly of claim 24, wherein the outer cap is formed of a material comprising a ceramic.

28. The virtual ablation electrode assembly of claim 24, wherein the outer cap is formed of a material comprising a fluoro-polymer.

29. The virtual ablation electrode assembly of claim 24, wherein the outer cap is formed of a material comprising an epoxy resin.

30. The virtual ablation electrode assembly of claim 24, wherein the plurality of pores are arrayed longitudinally along a length of the outer cap and circumferentially 360 degrees around the outer cap.

31. The virtual ablation electrode assembly of claim 25, wherein the plurality of pores are arrayed longitudinally along a length of the outer cap and circumferentially 360 degrees around the outer cap extending over the dome-shaped distal end region.

32. The virtual ablation electrode assembly of claim 24, wherein a maximum diameter of each of the plurality of pores is sized to prevent ingress of blood cells into the fluid chamber from the cap outer surface.

33. The ablation catheter of claim 24, wherein a maximum diameter of each of the plurality of pores is between approximately 0.0005 inch and 0.005 inch.

34. The virtual ablation electrode assembly of claim 24, wherein the plurality of pores is formed by a process selected from the group consisting of laser drilling, chemical etching and sintering.

35. The virtual ablation electrode assembly of claim 24, wherein a maximum distance between the exterior surface of the electrode and the cap inner surface is between approximately 0.003 inch and approximately 0.005 inch.

36. The virtual ablation electrode assembly of claim 24, wherein the exterior surface of the electrode includes extensions increasing a surface area of the exterior surface.

37. The virtual ablation electrode assembly of claim 36, wherein the extensions form a spiral coil.

38. The virtual ablation electrode assembly of claim 24, wherein the one or more spacers extend circumferentially about a proximal end of the electrode.

39. The virtual ablation electrode assembly of claim 24, wherein the one or more spacers extend distally from a distal end of the electrode.

40. The virtual ablation electrode assembly of claim 24, wherein one of the one or more fluid distribution branches passes through a distal end of the electrode.

41. The virtual ablation electrode assembly of claim 40, wherein the one of the one or more spacers extends distally from a distal end of the electrode.

42. The virtual ablation electrode assembly of claim 41, wherein the cap further includes a hole extending from the cap inner surface to the cap outer surface and generally aligned and in fluid communication with the one of the one or more fluid distribution branches.

43. The virtual ablation electrode assembly of claim 24, wherein a diameter of the fluid trunk of the electrode is between approximately 0.005 inch and approximately 0.030 inch.

44. The virtual ablation electrode assembly of claim 24, wherein a diameter of each of the one or more fluid distribution branches is between approximately 0.005 inch and approximately 0.030 inch.

* * * * *